United States Patent [19]

Holsopple

[11] Patent Number: 4,556,510

[45] Date of Patent: Dec. 3, 1985

[54] TRANSPARENT LIQUID SHOWER SOAP

[75] Inventor: Peggy S. Holsopple, Camden County, N.J.

[73] Assignee: Hercules Incorporated, Wilmington, Del.

[21] Appl. No.: 617,670

[22] Filed: Jun. 6, 1984

Related U.S. Application Data

[63] Continuation-in-part of Ser. No. 509,749, Jun. 30, 1983, abandoned.

[51] Int. Cl.$^4$ .................. C11D 1/12; C11D 3/37; C11D 17/08
[52] U.S. Cl. .................. 252/547; 252/173; 252/174.17; 252/174.23; 252/546; 252/550; 252/552; 252/555; 252/557; 252/558; 252/DIG. 2; 252/DIG. 5; 252/DIG. 13; 252/DIG. 14; 252/DIG. 15
[58] Field of Search .............. 252/174.17, 174.18, 252/DIG. 2, DIG. 5, DIG. 13, DIG. 14, DIG. 15, 173, 96

[56] References Cited

U.S. PATENT DOCUMENTS

| | | | |
|---|---|---|---|
| 4,072,632 | 2/1978 | Reed | 252/541 |
| 4,323,467 | 4/1982 | Fu | 252/106 |
| 4,330,438 | 5/1982 | Dierassi et al. | 424/70 |
| 4,338,211 | 7/1982 | Stiros | 252/142 |
| 4,414,144 | 11/1983 | Liebowitz et al. | 252/552 |
| 4,420,410 | 12/1983 | Huttinger | 252/117 |
| 4,434,089 | 2/1984 | Billington et al. | 252/547 |
| 4,472,297 | 9/1984 | Bolich, Jr. et al. | 252/550 |
| 4,491,539 | 1/1985 | Hoskins et al. | 252/174.17 |

FOREIGN PATENT DOCUMENTS 1955557 5/1971 Fed. Rep. of Germany .
1235292 6/1971 United Kingdom .

OTHER PUBLICATIONS

Natrosol ® Hydroxyethylcellulose A Nonionic Water-Soluble Polymer, Hercules Incorporated, Rev. 10-80, Wilmington, Delaware 19899.

Primary Examiner—Prince E. Willis
Assistant Examiner—Hoa Van Le
Attorney, Agent, or Firm—Joanne L. Horn

[57] ABSTRACT

Disclosed is a transparent liquid composition suitable for use as a soap, primarily a shower soap, which is thickened with a water-soluble polymer, such as, hydroxyethyl cellulose or hydroxypropyl guar.

14 Claims, No Drawings

TRANSPARENT LIQUID SHOWER SOAP

This application is a continuation-in-part of the application, Ser. No. 509,749, filed June 30, 1983, now abandoned, for Transparent Liquid Shower Soap.

This invention relates to transparent liquid compositions suitable for use as a shower soap. More specifically, this invention refers to such compositions having a surface active ingredient concentration of less than 15% wherein a water-soluble polymer is employed to impart desirable properties thereto.

Liquid compositions useful as shower soaps are newcomers in the cosmetic field. Basically, liquid shower soaps were developed by combining some of the technology of liquid hand soaps with some of the technology of bath gels. Unfortunately, both the liquid hand soaps and the bath gels have disadvantages in the shower environment. Liquid hand soaps are low lathering and tend to dry and defat the skin. Bath gels are too viscous and are likewise slow to lather.

Generally, shower soaps contain a detergent, a primary lathering agent, and a non-polymeric primary thickening agent in a water vehicle as the principal ingredients.

Up until the present time, liquid shower soaps have been thickened with a high concentration of surface active agents, with sodium chloride or with a combination of surfactants and sodium chloride. As a general rule, surfactants which are mild to the skin are very poor lathering agents and ineffective cleaners, whereas surfactants which give high sudsing are harshest to the skin and highest in skin oil removal (defatting). High concentrations of surfactants, i.e., 20% to 25% of surfactants, are generally used to increase the lathering characteristics of the liquid soap; however, this is at the expense of increased skin dryness. Usually, sodium chloride is not used at all when a high concentration of one or more surfactants is employed. Sodium chloride tends not only to dry out the skin, but to be highly irritating to the eyes.

Thus, there is a need for a liquid soap having improved lathering characteristics and reduced surfactant concentration which will gently cleanse the skin without drying the skin after routine use. Soaps which do not dry out the skin surfaces, but tend to soften and soothe surface tissues are said to be emollient. Thus, the more emollient a soap the milder it is to the skin surfaces. Further, the more emollience a soap has the less likely it is to irritate the eyes.

According to this invention, there is provided a liquid soap composition containing a water-soluble polymer as the primary thickening agent which liquid soap composition exhibits improved lather characteristics, imparts superior lubricity and emollience to the skin surfaces, and contains less than 15% of surface active ingredients. Specifically, this invention relates to a liquid shower soap composition based on an anionic surfactant detergent, a primary lathering agent selected from the group consisting of anionic and amphoteric surfactants or mixtures thereof, and a water-soluble hydroxyethyl cellulose or water-soluble hydroxypropyl guar containing clearly defined amounts of the hydroxyalkyl group as the principal or essential components, all of which are dissolved in a water vehicle.

More specifically, the hydroxyethyl cellulose is one having a hydroxyethyl substitution from about 1.8 to about 3.7 M.S., preferably from about 2.0 to about 3.0 M.S., and a water viscosity from about 400 centipoise (cps.) to about 5000 cps. at 25° C. at 1% concentration at 30 rpm. The molecular substitution (M.S.) for hydroxyethyl cellulose is defined as the average number of moles of hydroxyethyl substituent groups present per anhydroglucose unit.

The hydroxpropyl guar is one having a hydroxypropyl substitution from about 0.35 to about 1.0 M.S., preferably from about 0.5 to about 0.9 M.S. The molecular substitution (M.S.) for hydroxypropyl guar is defined as the average number of moles of hydroxypropyl substituent groups present for anhydrohexose unit.

In commercial practice, the concentrations of the principal ingredients can and do vary widely. In most commercial formulations the principal ingredients, which should add up to 100%, are within the following concentration ranges:

| Ingredients | Percent by weight based on the principal ingredients |
| --- | --- |
| Anionic surfactant detergent | 50–90 |
| Primary lathering agent | 10–50 |
| Primary thickener | 0.5–15 |

Water, at a concentration of from about 75% to about 88% by weight of the total composition, is the vehicle for the ingredients.

The hydroxyethyl cellulose which can be used as a primary thickener in the compositions of this invention is prepared by reacting ethylene oxide with cellulose and a strongly alkaline medium. Specific techniques for carrying out the etherification are well known in the art and any known procedure can be employed. See, for example, Whistler, R. L. & BeMiller, J. N., *Industrial Gums*, p. 650 (2ed. 1973). The hydroxyethyl cellulose useful in the practice of this invention is also available commercially from Hercules Incorporated.

The hydroxypropyl guar gum can be prepared by the method of U.S. Pat. No. 3,700,612.

The concentration of hydroxyethyl cellulose or the hydroxypropyl guar in the composition of this invention is from about 0.5% to about 15% by weight based on the principal ingredients. Desirably the water-soluble polymeric thickener is present at a concentration from about 5% to about 10%.

The detergent is an anionic surfactant, the key functional property of which is detergency. Suitable anionic surfactants which mainly function as detergents include (1) alkylbenzenesulfonates of the formula:

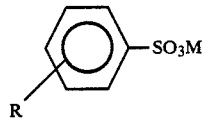

where R is dodecyl and M is sodium, calcium, triethanolammonium, and isopropylammonium; (2) alpha-olefinsulfonates of the formula:

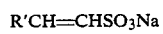

where R' is 10–18 carbon atoms and mixtures thereof, preferably 10–16 carbon atoms and mixtures thereof; and (3) alkyl sulfates of the formula R"OSO₃M' where R" is lauroyl and M' is sodium, potassium, ammonium, diethanolammonium, and triethanolammonium. The preferred anionic surfactant is a mixture of sodium alpha olefin sulfonates containing 10 to 14 carbon atoms.

The primary lathering agent can be an anionic or amphoteric surfactant or mixtures thereof which function chiefly as foaming or lathering agents. Such anionic surfactants include (1) dialkyl sulfosuccinates of the formula: $RO_2CCH_2CH(SO_3Na) CO_2R$, where R is lauroyl or myristyl; (2) N-acyl-sarcosinates of the formula: $R'CON(CH_3)CH_2CO_2Na$, where $R'CO-$ is lauroyl and cocoyl; (3) sodium N-acyl-N methyltaurates of the formula: $R''CON(CH_3)CH_2CH_2SO_3Na$, where $R''CO$ is acyl, such as oleyl, cocoyl, palmitoyl and tall oil; and (4) sodium cocoylisothionate. Typical amphoteric surfactants include amidopropylbetaines of the formula: $R'''CONHCH_2CH_2CH_2N^+(CH_3)_2CH_2CO_2^-$, where $R'''CO$ is cocoyl and lauroyl. The preferred lathering agent is sodium lauroyl sarcosinate.

In addition to the principal ingredients mentioned above, a typical liquid shower soap will frequently contain other conventional additives, such as a secondary thickener, a secondary lathering agent, chelating agents, preservatives, colorants, and fragrances.

Coco methanolamide, a nonionic surfactant, is a suitable secondary thickener and secondary lathering agent. The disodium salt of ethylenediamine tetracetic acid (EDTA) is a typical chelating agent. Suitable preservatives include methylparaben, propylparaben, formaldehyde and imidazolidinyl urea.

The following examples are illustrative of the invention. All parts and percentages used in this disclosure are by weight unless otherwise indicated.

EXAMPLE 1

The following example illustrates a specific embodiment of the liquid shower soap composition of this invention and how to prepare it.

A liquid shower soap composition using the formulations set forth in Table 1 is prepared by placing the water in a tank fitted with a marine propeller stirrer. Stirring is commenced. The preservative is added to the water and stirring continued at room temperature until the preservative is dissolved. The thickener is then added and stirring continued at room temperature until the thickener dissolves.

The resulting aqueous mixture is then transferred to a tank equipped with a paddle stirrer. The mixture of alpha olefin sulfonates is added to the aqueous mixture and stirred until the sulfonate mixture is dissolved. The sodium lauroyl sarcosinate is then added and stirred until it is dissolved.

While maintaining agitation, the aqueous mixture is heated up to 70° C. The coco methanolamide is then added and stirred until dissolved. The mixture is allowed to cool to room temperature, at which point the EDTA is added and stirred until dissolved.

TABLE 1

| Ingredients | Percent by Weight of the Total Composition |
| --- | --- |
| A mixture of sodium alpha-olefin sulfonates having 10 to 14 carbon atoms | 8.0 |
| Sodium lauroyl sarcosinate | 3.0 |
| Hydroxyethyl cellulose (2.5 Hydroxyethyl M.S.; 3000 cps. water viscosity at 25° C. and 1% concentration) | 1.0 |
| Distilled $H_2O$ | 84.7 |
| Cocamide Methanolamide | 3.0 |
| Disodium salt of ethylenediamine tetraacetic acid (EDTA) | 0.20 |
| Methylparaben | 0.1 |

The composition is clear yellow in appearance, has a Brookfield viscosity of 7680 centipoise at 25° C. as measured by a Brookfield LVT viscometer at 30 rpm, and has a surface active ingredient concentration of 14%.

EXAMPLE 2

This example illustrates another specific embodiment of the liquid shower soap composition of this invention.

The procedure of Example 1 and the formulation of Table 1 are used except that a hydroxypropyl guar having 0.5 hydroxypropyl M.S. is used instead of the hydroxyethyl cellulose. The composition has a translucent appearance, a viscosity of 7680 centipoise at 25° C. at 30 rpm, and has a surface active ingredient concentration of 14%.

EXAMPLE 3

This example illustrates another specific embodiment of the liquid shower soap composition of this invention.

The procedure of Example 1 and the formulation of Table 1 are used except that a hydroxypropyl guar having 0.9 hydroxypropyl M.S. is used instead of the hydroxyethyl cellulose. The composition is translucent in appearance, has a viscosity of 7800 centipoise at 25° C. 30 rpm, and a surface active ingredient concentration of 14%.

EXAMPLE 4

This example illustrates another specific embodiment of the liquid shower soap composition of this invention.

The procedure of Example 1 and the formulation of Table 1 are used except that a hydroxyethyl cellulose having 2.6 hydroxyethyl M.S. and a water viscosity of 2000 cps. at 25° C. and 1% concentration is used in place of a hydroxyethyl cellulose having 2.5 hydroxyethyl M.S. and a water viscosity of 3000 cps. at 25° C. and 1% concentration, and except that no EDTA is added. The composition is clear in appearance, has a viscosity of about 7000 centipoise at 25° C. 30 rpm, and has a surface active ingredient concentration of 14%.

The compositions of this invention are readily dispersed by a pump, capable of being ejected in a quick stream from a narrow orifice, and freely pourable from a suitable container.

Thus, this invention provides useful liquid shower soap compositions having improved lathering characteristics, increased emollience, and a surface active ingredient concentration of less than 15%.

Features, advantages and other specific embodiments of this invention will become readily apparent to those exercising ordinary skill in the art after reading the foregoing disclosures. In this regard, while specific embodiments of this invention have been described in considerable detail, variations and modifications of these embodiments can be effected without departing from the spirit and scope of the invention as disclosed and claimed.

What I claim and desire to protect by letters patent is:

1. A liquid soap composition consisting essentially of, in an aqueous medium, by weight of its principal ingredients,
   (a) from about 50% to about 90% of an anionic surfactant detergent selected from the group consisting of (i) alkylbenzenesulfonates of the formula:

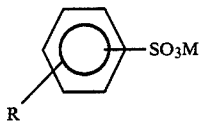

where R is dodecyl and M is sodium, calcium, triethanolammonium, and isopropylammonium; (ii) alpha-olefinsulfonates of the formula:

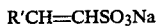

R'CH=CHSO₃Na where R' is 10-18 carbon atoms and mixtures thereof; and (iii) alkyl sulfates of the formula R"O-SO₃M' where R" is lauroyl and M' is sodium, potassium, ammonium, diethanolammonium, and triethanolammonium;
   (b) from about 10% to about 50% of a primary lathering agent selected from the group consisting of (i) dialkyl sulfosuccinates of the formula RO₂CCH₂CH(SO₃Na) CO₂R, where R is lauroyl or myristyl, (ii) N-acyl-sarcosinates of the formula R'CON(CH₃)CH₂CO₂Na, where R'CO— is lauroyl and cocoyl, (iii) sodium N-acyl-N-methyltaurates of the formula R"CON(CH₃)CH₂CH₂SO₃Na, where R"CO is acyl, (iv) sodium cocoylisothionate, (v) amidopropylbetaines of the formula R'''CONHCH₂CH₂CH₂N+(CH₃)₂CH₂CO₂, where R'''CO is cocoyl and lauroyl, and (vi) mixtures thereof;
   (c) from about 0.5% to about 15% of a primary water-soluble polymer thickener selected from the group consisting of hydroxyethylcellulose and hydroxypropyl guar as its principal ingredients wherein the total of (a), (b), and (c) is 100% of the principal ingredients; and
   (d) water from about 75% to about 88%.

2. The composition of claim 1 wherein the water-soluble polymer is a hydroxyethyl cellulose having a hydroxyethyl substitution of about 1.8 to about 3.7 M.S. and a water viscosity from about 400 cps. to about 5000 cps. at 25° C. and 1% concentration at 30 rpm.

3. The composition of claim 1 wherein the water-soluble polymer is a hydroxypropyl guar having a hydroxypropyl substitution from about 0.35 to about 1.0 M.S.

4. The composition of claim 2 wherein the water-soluble polymer is present at a concentration from about 5% to about 10%.

5. The composition of claim 3 wherein the water-soluble polymer is present at a concentration from about 5% to about 10%.

6. The composition of claim 1 wherein the water-soluble polymer is present at a concentration from about 5% to about 10%.

7. The composition of claim 1 wherein component (a) is anionic surfactant detergent (i).

8. The composition of claim 1 wherein component (a) is anionic surfactant detergent (ii).

9. The composition of claim 1 wherein component (a) is anionic surfactant detergent (iii).

10. The composition of claim 1 wherein component (b) is anionic surfactant detergent (i).

11. The composition of claim 1 wherein component (b) is anionic surfactant detergent (ii).

12. The composition of claim 1 wherein component (b) is anionic surfactant detergent (iii).

13. The composition of claim 1 wherein component (b) is anionic surfactant detergent (iv).

14. The composition of claim 1 wherein component (b) is anionic surfactant detergent (v).

* * * * *